(12) United States Patent
Ford

(10) Patent No.: US 9,188,598 B2
(45) Date of Patent: Nov. 17, 2015

(54) SAMPLE LOADING CAROUSEL

(75) Inventor: Gordon C. Ford, St. Joseph, MI (US)

(73) Assignee: Leco Corporation, St. Joseph, MI (US)

(*) Notice: Subject to any disclaimer, the term of this patent is extended or adjusted under 35 U.S.C. 154(b) by 365 days.

(21) Appl. No.: 13/402,192

(22) Filed: Feb. 22, 2012

(65) Prior Publication Data

US 2012/0213678 A1 Aug. 23, 2012

Related U.S. Application Data

(60) Provisional application No. 61/445,649, filed on Feb. 23, 2011.

(51) Int. Cl.
| | | |
|---|---|---|
| *G01N 5/02* | (2006.01) | |
| *G01N 35/02* | (2006.01) | |
| *G01N 1/22* | (2006.01) | |
| *F27B 17/02* | (2006.01) | |
| *G01N 31/12* | (2006.01) | |

(52) U.S. Cl.
CPC ............... *G01N 35/025* (2013.01); *F27B 17/02* (2013.01); *G01N 2001/2235* (2013.01)

(58) Field of Classification Search
CPC ............ F27B 17/02; F27D 2003/0016; G01N 35/025
USPC ............................................. 422/78, 551, 561
See application file for complete search history.

(56) References Cited

U.S. PATENT DOCUMENTS

| | | | |
|---|---|---|---|
| 4,371,971 A | | 2/1983 | Bredeweg |
| 5,372,500 A | * | 12/1994 | Valentian ...................... 432/241 |
| 5,549,473 A | * | 8/1996 | Valentian ...................... 432/239 |
| 6,291,802 B1 | | 9/2001 | Ford |
| 7,402,280 B2 | | 7/2008 | Ford |
| 7,404,670 B2 | * | 7/2008 | Willis ............................. 374/14 |
| 2004/0175295 A1 | * | 9/2004 | Garcia ........................... 422/78 |

OTHER PUBLICATIONS

Wooller, Matthew et al. "The elemental analyzer sample carousel: loading an autosampler made easy," Rapid Communications in Mass Spectrometry. 2001, 15, p. 1957-1959.*

* cited by examiner

*Primary Examiner* — Dennis M White
*Assistant Examiner* — Bryan Kilpatrick
(74) *Attorney, Agent, or Firm* — Price Heneveld LLP

(57) ABSTRACT

An improved sample handling carousel is mounted to an analytical furnace at an acute angle and includes sample holding cavities which are readily visible at eye level to an operator. The rotary carousel can be easily removed from a stepwise driven drive shaft for filling the carousel at a remote location, such as a weighing station, or can be filled directly while mounted on the drive shaft. A tray is positioned below the carousel and has a slot for dropping a sample when one of the sample holding cavities aligns with the slot in the tray. In a preferred embodiment of the invention, the carousel is made of aluminum or a transparent polymeric material, such as acrylic.

20 Claims, 8 Drawing Sheets

SAMPLE LOADING CAROUSEL

CROSS-REFERENCE TO RELATED APPLICATIONS

This application claims priority under 35 U.S.C. §119(e) and the benefit of U.S. Provisional Application No. 61/445,649 entitled SAMPLE LOADING CAROUSEL, filed on Feb. 23, 2011, by Gordon C. Ford, the entire disclosure of which is incorporated herein by reference.

BACKGROUND OF THE INVENTION

The present invention relates to a sample introduction assembly for loading samples into analytical crucibles for subsequent fusion and analysis.

An analytical furnace employs relatively small pin, chip, or other samples, typically in sizes of from about 1 mg to about 1 g. Graphite crucibles are employed for resistance heating of a crucible directly when placed between a pair of electrodes. Ceramic crucibles are employed in furnaces in which heating is by an induction field provided by an RF coil. In either furnace, it is necessary initially to outgas the crucible and assure no contaminant gases are mixed with the specimen gases during loading of the sample.

In several prior art systems, it is necessary to open the combustion chamber area after the outgassing to gain access to a crucible for insertion of a sample to be analyzed. In doing so, the crucible is exposed to atmospheric gases which can contaminate the crucible to an extent that the analytical results can be adversely effected. In order to prevent the introduction of contaminants, one solution has been to provide a sample loading mechanism which allows the introduction of a sample into a movable hopper which is subsequently sealed and the area purged with an inert gas. The jaws of the hopper are subsequently opened to allow admission of the sample into the crucible through an electrode assembly in resistance furnaces. U.S. Pat. No. 4,371,971 discloses such an apparatus. Although preventing a direct communication path with the atmosphere during admission of the sample, it may still allow a small amount of atmospheric gases to enter the combustion chamber during the sample loading operation. Improved sample loading mechanisms have been designed for introducing samples into a crucible while minimizing the introduction of contaminants into the furnace. U.S. Pat. No. 6,291,802 discloses one such system. U.S. Pat. No. 7,402,280 also discloses a crucible and sample loading system in which a plurality of samples are mounted in stacked carousels and are selectively transported from the carousel to the analytical furnace.

In order to automate the successive analysis of multiple samples, a horizontally extending sample holding carousel has also been employed and positioned above the sample drop assembly to introduce samples into the sample drop assembly shown, for example, in the above '802 patent. In such system, the sample holding carousel is positioned above the furnace, however, it is somewhat difficult for an operator to load the carousel while mounted to the furnace without the use of a step stool or other means for elevating the operator. There remains a need, therefore, for an improved sample handling apparatus which is easier to use and preferably one which can contain multiple samples for successive automatic introduction of samples into a combustion furnace for analysis.

SUMMARY OF THE INVENTION

The system of the present invention provides an improved sample handling carousel which is mounted to an analytical furnace at an acute angle. The carousel includes sample holding cavities which are readily visible at eye level to an operator. The rotary carousel can be easily removed from a stepwise driven shaft for filling the carousel at a remote location, such as a weighing station, or can be filled directly while mounted on the rotary drive shaft.

In a preferred embodiment of the invention, the carousel is mounted to the furnace at an acute angle to a horizontal plane of about 45°. The sample holding cavities are formed at an angle of about 30° to the rotary axis of the carousel, such that samples are held in sample holding cavities around the entire periphery of the disk-shaped carousel. A tray is positioned below the carousel and has a slot for dropping a sample through the tray when one of the sample holding cavities aligns with the slot in the tray. In a preferred embodiment of the invention, the carousel is made of a transparent polymeric material, such as acrylic, such that the samples are readily visible to the operator. A hub couples the carousel to a drive motor, such that the carousel and tray can be easily removed and replaced.

These and other features, objects and advantages of the present invention will become apparent upon reading the following description thereof together with reference to the accompanying drawings.

DETAILED DESCRIPTION OF THE PREFERRED EMBODIMENT

Figure 1:
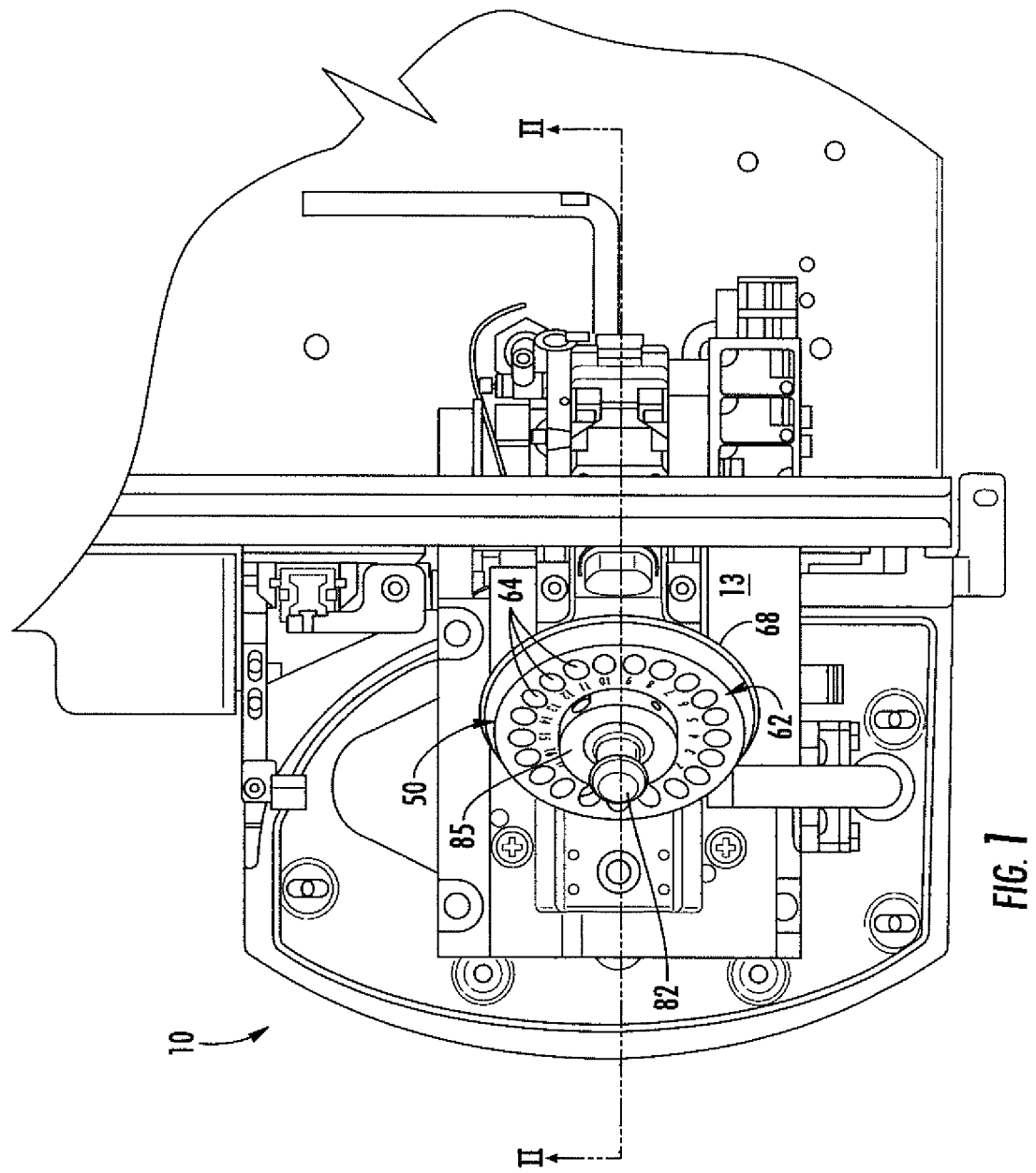
FIG. 1 is a top plan view of the furnace section of an analyzer showing the improved sample loading carousel of the present invention.
Figure 2:
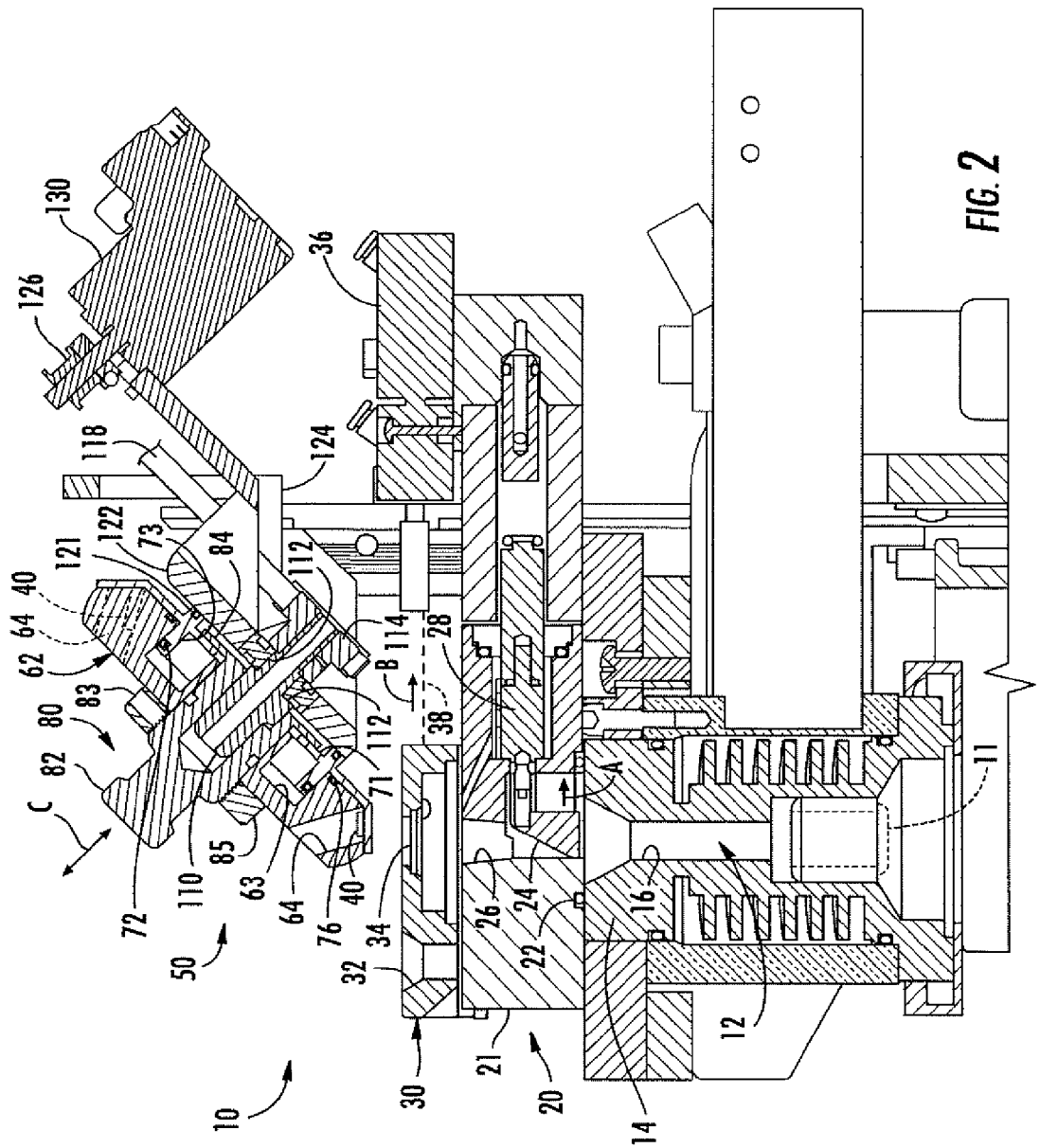
FIG. 2 is a cross-sectional view taken along section line II-II of FIG. 1 of the carousel and upper section of the furnace.

Referring initially to FIG. 1, there is shown a section of a furnace for an analyzer, such as a Leco Model ONH836. The analytical furnace 10 is a resistance furnace which includes, as seen in FIG. 2, a furnace area 12 including an upper electrode 14, which matingly receives a lower electrode (not shown) holding a graphite crucible in alignment with the open cylindrical passageway 16 of upper electrode 14. The crucible placement is illustrated by the schematic phantom crucible 11 in FIG. 2 and is positioned to receive samples, such as pin, chip or other forms of samples to be analyzed. The construction of furnace 10 can be substantially identical to the furnace used in analyzer Model No. ONH836, commercially available from Leco Corporation of St. Joseph, Mich. The electrode 14 can be of the type disclosed in U.S. patent application Ser. No. 13/358,096 filed Jan. 25, 2012, entitled VACUUM CLEANING STRUCTURE FOR ELECTRODE FURNACE, the disclosure of which is incorporated herein by reference. Above the furnace, there is positioned a sample drop assembly 20 of the type described in U.S. Pat. No. 6,291,802, the disclosure of which is incorporated herein by reference.

The sample drop assembly 20 (FIG. 2) includes a sealed coupling to the upper surface of electrode 14 utilizing an O-ring seal 22 and a sliding gate 24 which selectively closes off the communication opening 26 formed through the block 21 of the sample drop assembly 20 and is aligned with passageway 16 in the upper electrode 14. A solenoid 28 selectively moves the gate 24 between a closed position, shown in FIG. 2, and a position to the right, as indicated by arrow A, for opening the discharge end of opening 26, allowing a sample positioned therein to drop into the crucible 11 through passageway 16 in electrode 14.

Above the sample drop assembly 20, there is provided a sliding block assembly 30 which includes a tapered funnel-shaped opening 32 at its upper end and an enclosed viewing port 34 adjacent funnel opening 32. Assembly 30 is coupled to a double acting pneumatic cylinder 36 through a coupling represented by dashed lines 38 to move between a position shown in FIG. 2 during an analysis of a sample and to the right, as shown by arrow B in the figure, when introducing a sample, such that opening 32 aligns with opening 26 in sample drop assembly 20. Assemblies 20, 30 are described in greater detail in the above-identified '802 patent.

Figure 3:
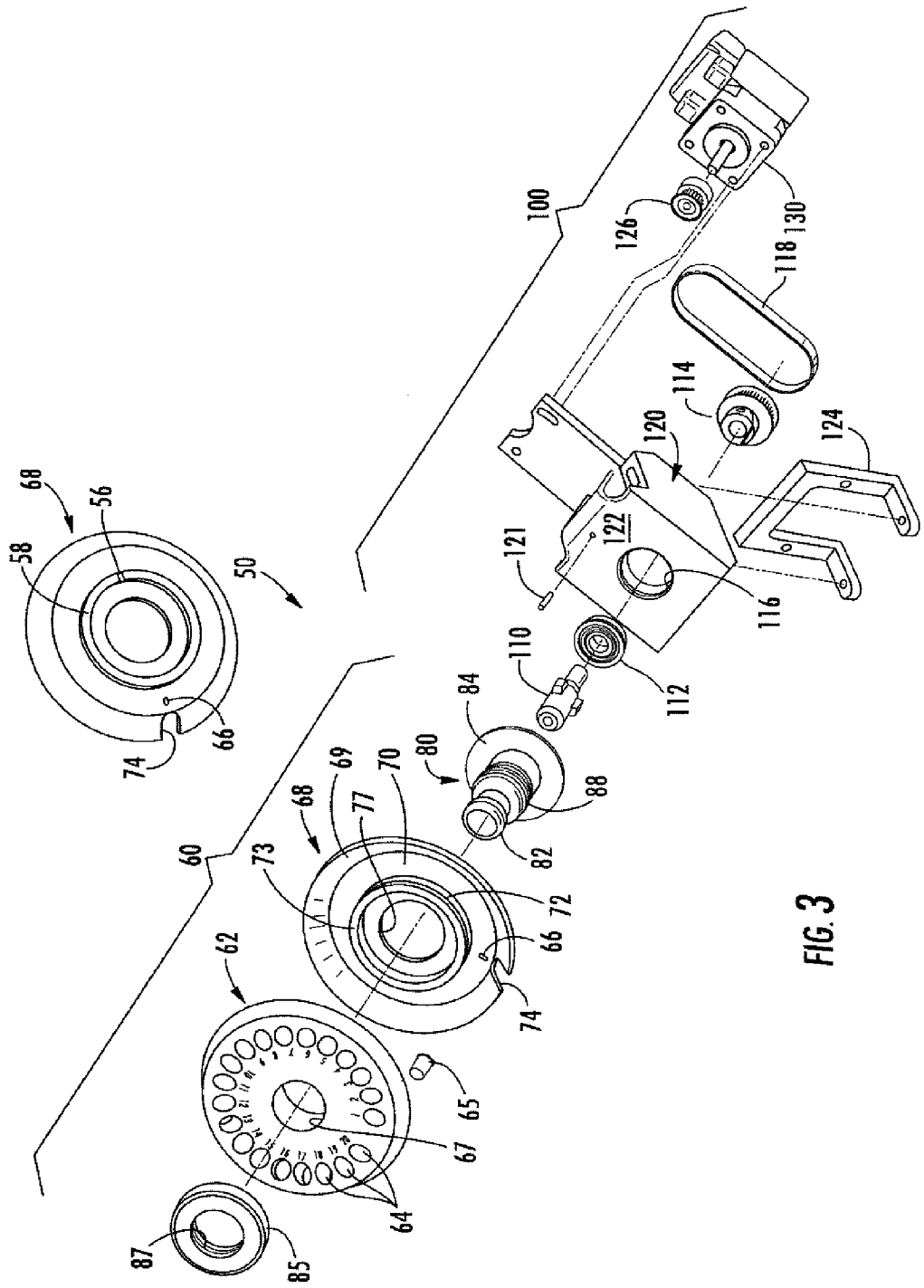
FIG. 3 is an exploded perspective view of the components of the sample loading carousel including an underside view of the carousel tray.
Figure 4:
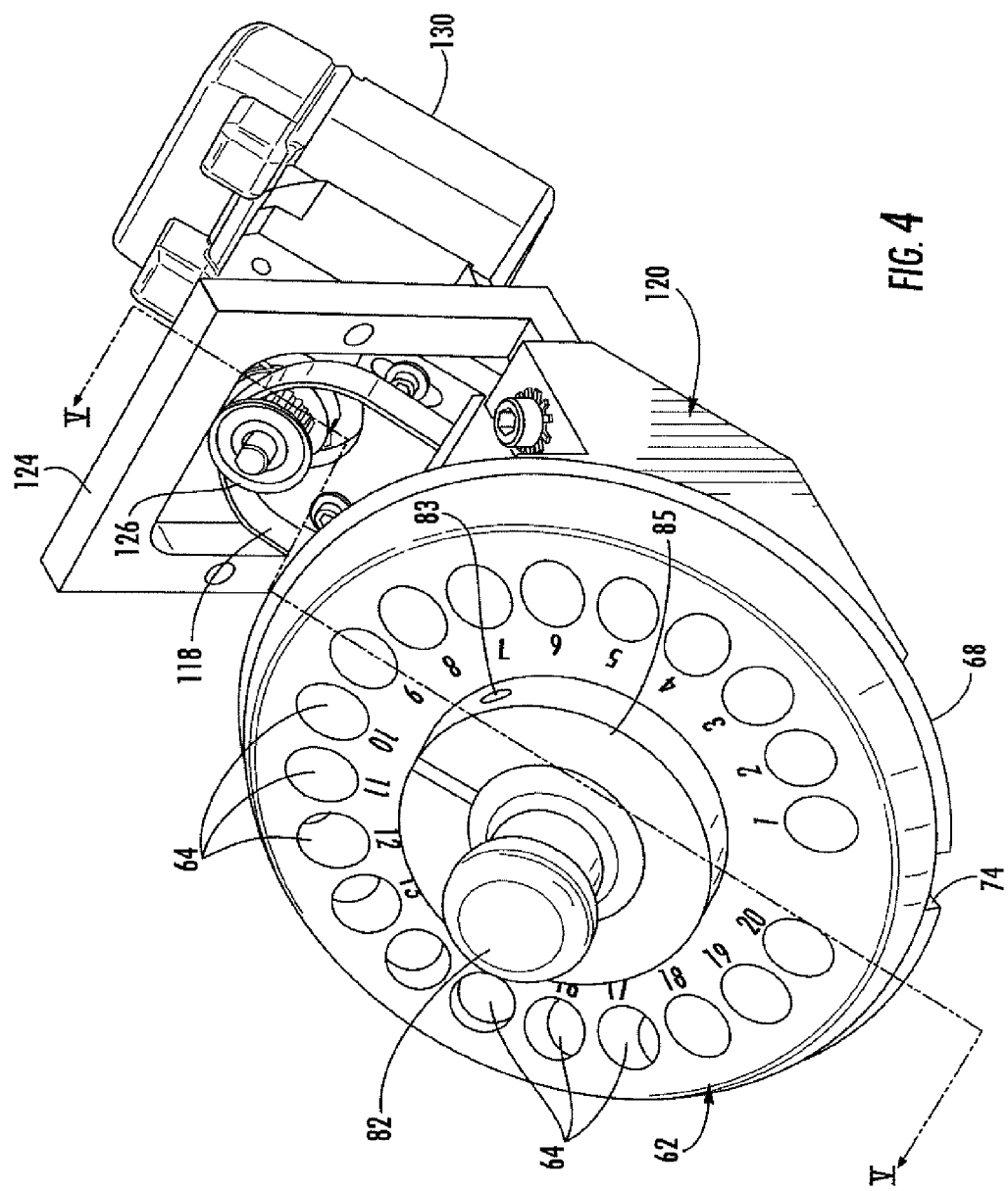
FIG. 4 is a perspective view of the assembled carousel.
Figure 5:
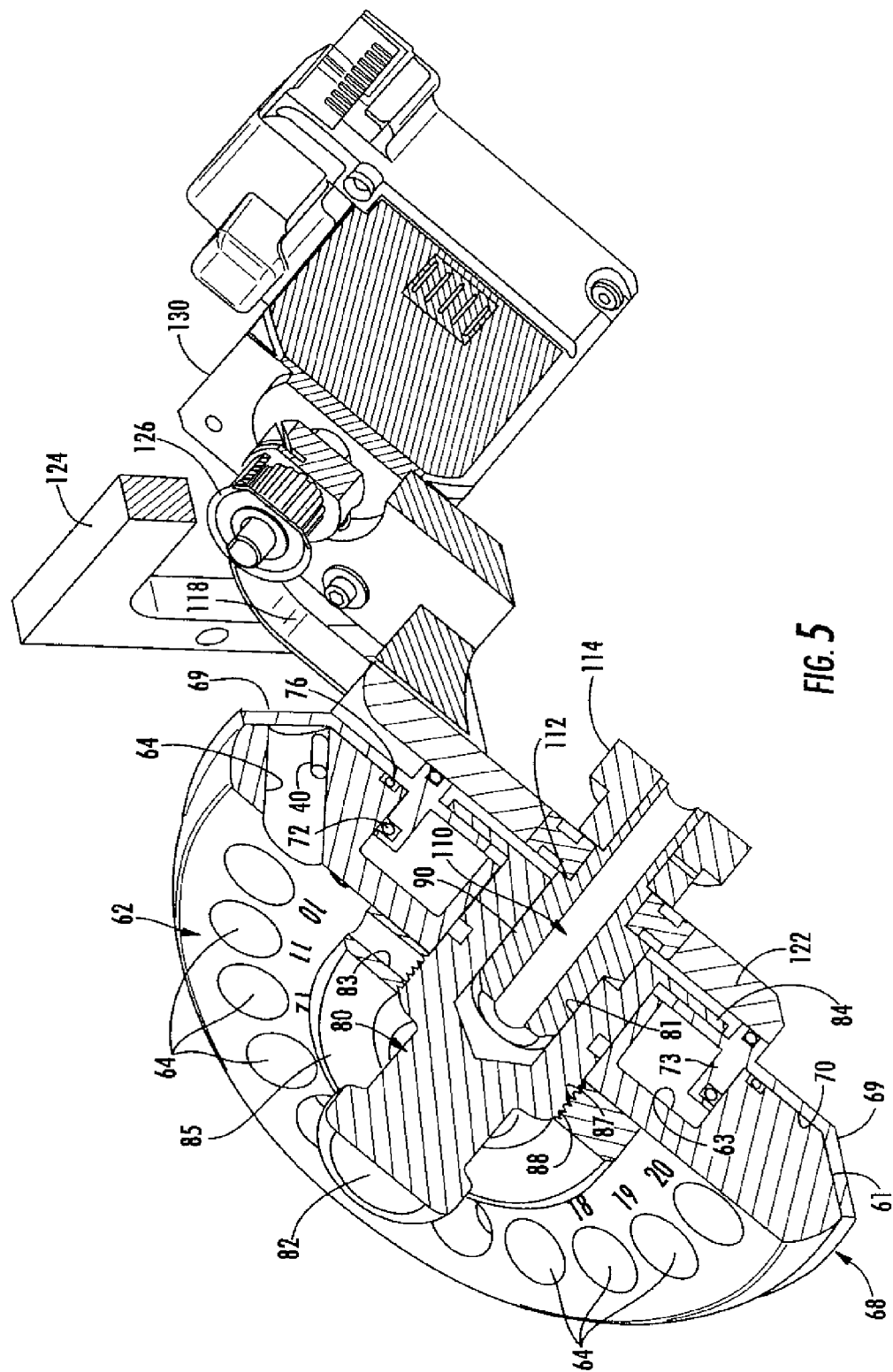
FIG. 5 is a cross-sectional view of the carousel assembly shown in FIG. 4, taken along section lines V-V in FIG. 4.

Positioned above furnace 10 and assemblies 20, 30 is the sample handling carousel assembly 50 of the present invention. The components of carousel assembly 50 are best seen in FIG. 3 and comprise two major subassemblies. The carousel components are identified by reference numeral 60 in FIG. 3, while the mounting and drive assembly are identified by reference numeral 100. The carousel comprises a disk-shaped member 62 with a plurality of cavities 64 located in equally spaced angular locations around the disk-shaped member 62. The cavities 64 are, as best seen in FIGS. 2 and 5, angled outwardly at approximately 30° to the rotational axis of member 62 identified by arrow C in FIG. 2. As seen in FIG. 2, when the carousel 50 is mounted to the furnace at a 45° angle to a horizontal plane, the cavities are tilted about 15° from vertical when a cavity is aligned with opening 32. A cavity on the opposite side of disk-shaped member 62 (i.e., at the uppermost position) is tilted downwardly about 15° from horizontal, as shown by cavity 64 in phantom lines in FIG. 2 and in solid lines in FIG. 5. This allows pins 40 or other samples placed within the cavities to remain in the cavities, by gravity, as the carousel 50 is rotated with the samples contained between the cylindrical walls of the angled cylindrical cavities 64 and the underlying tray 68, as best seen in FIGS. 2 and 5. Thus, the cavity numbered 9 shown in FIG. 5, for example, is slightly inclined downwardly allowing the sample 40 to remain in place under the influence of gravity as the carousel is rotated. In the embodiment shown, disk-shaped carousel member 62 includes twenty angularly spaced (about 17°) cavities for receiving twenty samples and a blank space between cavities numbered 1 and 20 (FIGS. 3 and 4).

The underside of the disk-shaped member 62 includes a spring-ball alignment pin 65 (FIG. 3) which engages an aperture 66 in the cupped-shaped backing tray 68. This pin and aperture allow the carousel and tray to remain aligned when being moved from a weigh station to the furnace. When the carousel is rotated, pin 65 releases from aperture 66 and rides on the floor 70 (FIG. 3) of tray 68. Tray 68 has an edge 69 which is formed at the same angle as beveled outer edge 61 of disk-shaped carousel member 62 and an annular floor 70 which rests under and aligns with the annular center section of the underside of disk-shaped carousel member 62, as best seen in FIG. 5. Tray 68 is rotationally stationary with a sample drop slot 74 aligned with funnel-shaped opening 32 of assembly 30 when assembly 30 is moved to a sample-receiving position to the right, as shown in FIG. 2. The tray 68 is indexed to motor mount plate 122 by pin 121 (FIG. 3) extending into slot 56 in annular spacing ring 58 on the underside of the tray 68, as seen in FIGS. 2 and 3, to prevent rotation of the tray as the carousel member 62 is rotated.

The underside of disk-shaped carousel member 62 includes an annular recess 63, which receives an annular upstanding shoulder 73 of tray 68 when positioned on the angled motor mounting plate 122, as best seen in FIGS. 2 and 5. Shoulder 73 of tray 68 includes an outer annular recess for receiving an O-ring 72 (FIGS. 2 and 3), which provides a slightly frictional interface between the stationary tray and the rotary carousel 62. The disk-shaped carousel 62 includes an annular recess on its lower surface facing the floor 70 of tray 68 for receiving an O-ring 76, which also allows controlled rotation of carousel 62 with respect to tray 68. The disk-shaped carousel member 62 and tray 68 each include a central opening 67 and 77, respectively, (FIG. 3), which are aligned with one another and which receives a carousel mounting hub 80 having a handling knob 82 at its outer end. Hub 80 has an annular shoulder 84 at its opposite end, which engages the underside of tray 68 when removing carousel assembly 50 from the furnace. The generally cylindrical body 86 of hub 80 extends through apertures 67 and 77 and threadably receives a locking clamp ring 85. Ring 85 is internally threaded at 87 and is threadably secured to the threads 88 on hub (FIGS. 3 and 5) for assembling carousel assembly 50 to drive assembly 100, as shown in FIGS. 1, 2, 4, and 5. This allows controlled stepwise motion of the carousel with respect to the tray 68. The clamp ring 85 is tightened down on the threaded end 88 of hub 80 sufficiently to provide a close coupling with carousel disk 62 and tray 68 and yet allow the carousel to rotate with respect to the tray 68. In one embodiment, the torque applied to rotate carousel 62 was from about 28 to about 32 ounce-inches. Clamp ring 85 has a radially extending threaded aperture 83 which allows a set screw to be threaded into the clamp ring and onto hub 80 for locking the clamp ring and hub in fixed relationship once the ring has been tightened the desired amount. A slight gap remains between the upper surface of shoulder 84 and the lower (bottom) surface of tray 68 to allow the hub 80 and carousel 62 to rotate with respect to the rotationally fixed tray. Ring 58 serves to provide a space 71 (FIG. 2) between the motor mounting plate 122 and annular shoulder 84 of hub 80 to allow rotation of the hub and connected carousel 62 with respect to the motor mounting plate 122.

Figure 6:
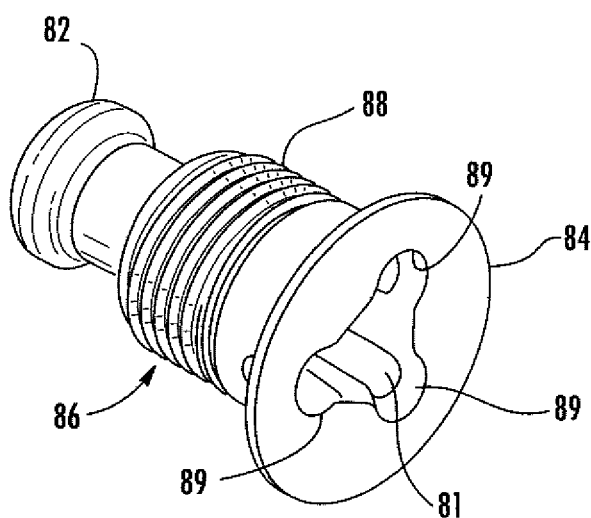
FIG. 6 is a bottom perspective view of the hub.
Figure 7:
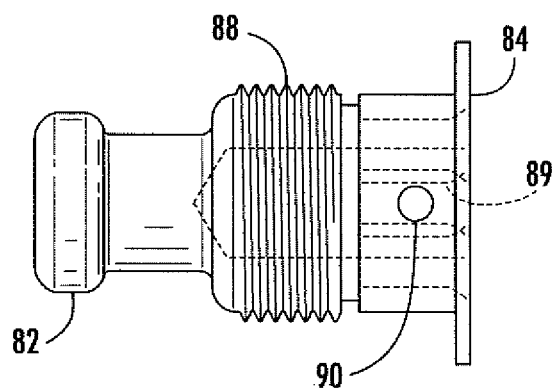
FIG. 7 is a side elevational view of the hub shown in FIG. 6.
Figure 8:
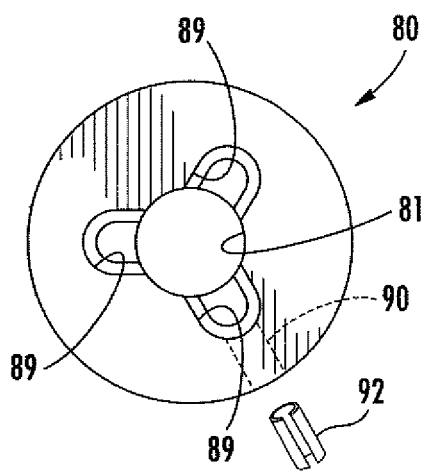
FIG. 8 is a bottom plan view of the hub.
Figure 9:
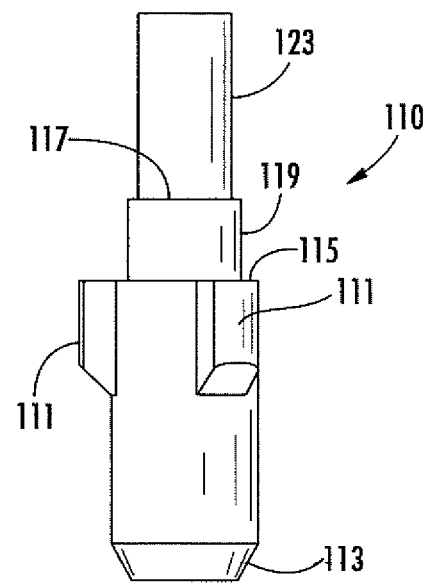
FIG. 9 is a side elevational view of the drive shaft.
Figure 10:
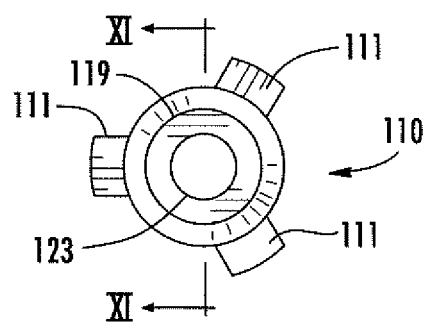
FIG. 10 is a top plan view of the drive shaft shown in FIG. 9.
Figure 11:
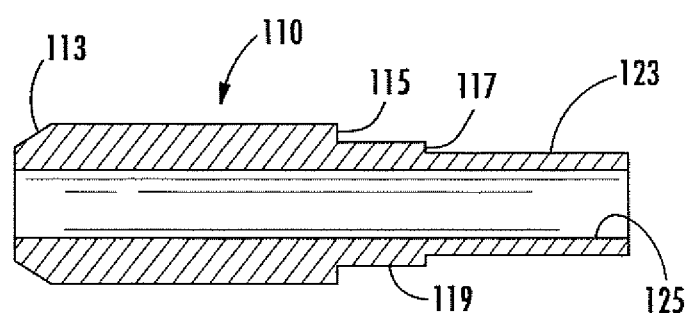
FIG. 11 is a cross-sectional view of the drive shaft taken along section lines XI-XI of FIG. 10.
Figure 12:
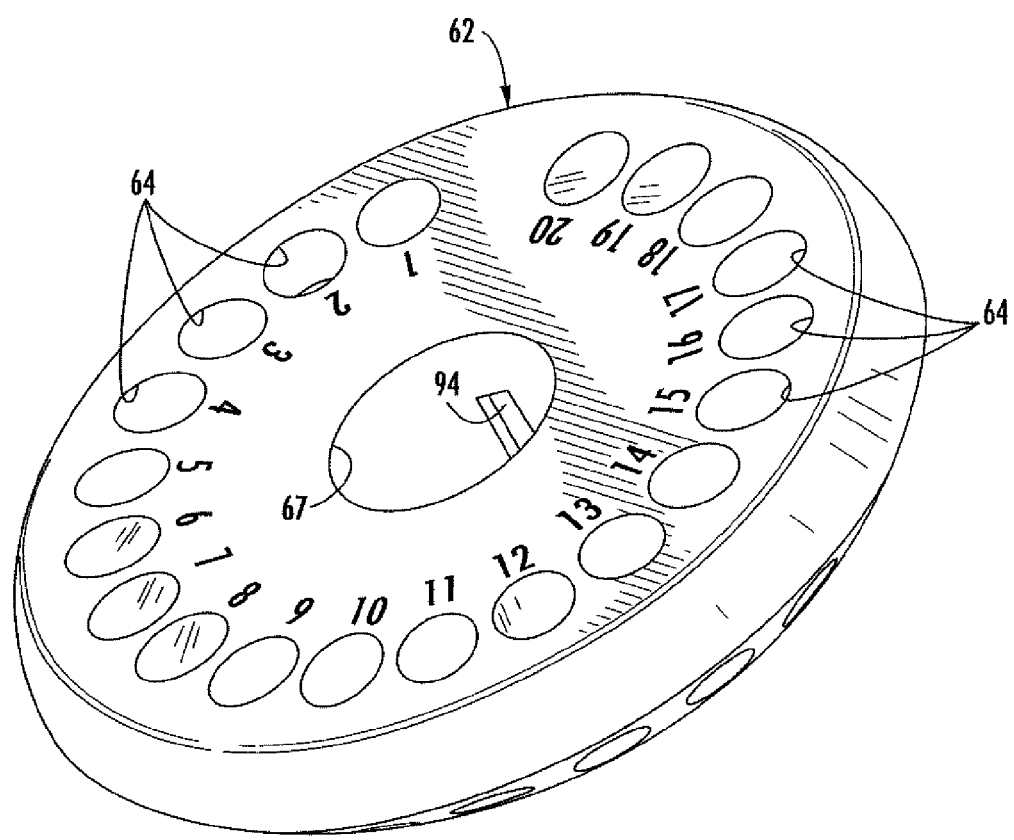
FIG. 12 is a top perspective view of the carousel.

Hub 80, as best seen in FIGS. 6-8, includes a central opening 81 in body 86 for receiving drive shaft 110, as best seen in FIGS. 2 and 5. Opening 81 includes three radially outwardly extending slots 89 (FIG. 8) spaced at 120° intervals, which interlock with and matingly receive three radially outwardly extending drive projections 111 spaced at 120° intervals on drive shaft 110, as best seen in FIGS. 9 and 10. Drive shaft 110 includes a chamfered end 113 (FIGS. 9 and 11) which facilitates mounting the hub 80 onto the drive shaft. Hub 80 includes an aperture 90 (FIG. 7) for receiving a dowel pin 92 (FIG. 8) which engages a slot 94 (FIG. 12) on the underside of carousel 62. Slot 94 is located at position zero and receives pin 92 to positively drive carousel 62. Drive shaft 110 is stepped at 115 and 117 (FIGS. 9 and 11) to define an annular shoulder 119, which is sized to engage bearing 112. End 123 of drive shaft 110 is dimensioned to fit within drive pulley 114 secured to end 123. Drive shaft 110 may also include an axially extending central opening 125 to reduce material and weight and to potentially act as a conduit for light.

The drive shaft 110 extends through bearing 112 in motor mounting plate 122, such that the carousel is driven by the rotation of drive shaft 110. Bearing 112 is received within an aperture 116 (FIG. 3) of mounting plate 122 of carousel mount 120. Mounting plate 122 is canted at an angle of approximately 45° to mount the carousel assembly 60 at about 45°, as best seen in FIGS. 2, 4, and 5. Mounting block 120 is secured by a bracket 124 (FIG. 3) to the furnace base 13, as seen in FIG. 1.

Drive shaft 110 is coupled to a drive pulley 114 which is driven by belt 118 coupled to a second drive pulley 126, in turn, coupled to a step drive motor 130. Motor 130 is pulse driven in a conventional manner to rotate belt 118 and rotate carousel member 62 coupled thereto in a stepwise manner an incremental distance corresponding to the angular spacing between adjacent cavities 64 to sequentially align one of the cavities 64 with sample drop opening 32. This sequentially feeds samples into the furnace for fusion and subsequent analysis.

The carousel assembly 60 is demountable from the drive shaft 110 by lifting knob 82 to pull the assembled components of carousel assembly 60 from the mounting and drive structure 100. This allows the carousel to be loaded with samples at a remote location, such as a weighing station, for weighing samples and entering them into the analyzer's computer control system. Also, by providing a carousel subassembly 60, a user may have two or more such subassemblies, such that, while one set of samples are being run, the operator can load another carousel, such that samples can be consecutively and continuously run. By the use of the indexing pins 65, 121 and related apertures 66, 56, respectively, a new loaded carousel assembly 60 can be readily placed on the drive shaft 110 and rotated to an indexed position without difficulty.

In order to introduce a sample into the furnace, cylinder 36 is actuated, sliding block 30 to a position in which opening 32 aligns with slot 74 in tray 68 and opening 26 in sample drop assembly 20 (FIG. 2). As the carousel member 62 is rotated by step motor 130 by a conventional drive circuit, a sample holding cavity 64 aligns with slot 74 and a sample drops into the sample drop assembly 20. Once the crucible containing furnace has been outgased, solenoid 28 is actuated and sliding gate 24 is then moved in a direction indicated by arrow A in FIG. 2 to drop the sample into the open mouth of the graphite crucible 11. The disk-shaped carousel member 62 in the preferred embodiment is made of metal, such as aluminum, although it can be made of a transparent polymeric material, such as an acrylic, to allow the samples contained therein to be readily visible to the operator.

With the system of the present invention, therefore, a carousel assembly is conveniently located at an angle such that pins or other samples can be added directly to the carousel while mounted on the instrument and visibly inspected by the operator and/or the carousel can be removed, filled at a remote location, and readily replaced on the mount and drive assembly. Thus, with the system of the present invention, the identification of samples in the carousel and introduction of samples into a fusion furnace is significantly easier to accomplish.

It will become apparent to those skilled in the art that various modifications to the preferred embodiment of the invention as described herein can be made without departing from the spirit or scope of the invention as defined by the appended claims.

The invention claimed is:

1. A sample handling carousel for an analytical furnace comprising:
    a disk-shaped carousel having an axis of rotation, said carousel including a plurality of angularly spaced sample holding cavities, wherein said sample holding cavities are formed outwardly at a first acute angle to the axis of rotation of said carousel, said carousel having a beveled outer edge through which said sample holding cavities extend;
    a mount for mounting said carousel to an analytical furnace at a second acute angle to a horizontal plane, and for rotating said carousel, wherein said second acute angle is greater than said first acute angle; and
    a tray positioned below said carousel, said tray including an edge formed at the same angle as said beveled outer edge of said carousel and positioned with respect to said carousel to selectively dose said sample holding cavities, said tray having a slot allowing a sample to be discharged from a sample holding cavity by dropping through said slot into the furnace when one of the sample holding cavities aligns with said slot in said tray.

2. The carousel as defined in claim 1 wherein said carousel is mounted to a stepwise driven rotary shaft for sequentially aligning sample holding cavities with said slot for sequentially dropping samples out of such cavities and into a furnace.

3. The carousel as defined in claim 2 and further including a mounting hub for coupling said carousel to said rotary shaft.

4. The carousel as defined in claim 1 wherein said carousel is made of one of metal and a transparent polymeric material.

5. The carousel as defined in claim 1 wherein said second acute angle is about 45°.

6. The carousel as defined in claim 5 wherein said first acute angle is about 30°.

7. The carousel as defined in claim 1 wherein said carousel is mounted to a stepwise driven rotary shaft and further includes a hub for removably coupling said carousel on said rotary shaft, said hub holding said tray and carousel together while allowing rotation of said carousel with respect to said tray.

8. A sample handling carousel for an analytical furnace comprising:
    a disk-shaped carousel having an axis of rotation and a beveled outer edge, said carousel including a plurality of angularly spaced sample holding cavities extending through said beveled outer edge, said cavities formed through said carousel at a first acute angle to the axis of rotation of said carousel;
    a stationary tray positioned below said carousel, said tray including an edge conforming to said beveled outer edge of said carousel and positioned to selectively close said sample holding cavities, said tray having a slot for releasing a sample from said sample holding cavity by allowing the sample to drop through said slot into the analytical furnace when said carousel is rotated with respect to said tray and one of the sample holding cavities aligns with said slot in said tray; and
    a mount for said carousel for mounting said carousel and tray to a furnace at a second acute angle to a horizontal plane, wherein said second acute angle is greater than said first acute angle.

9. The carousel as defined in claim 8 wherein said mount includes a stepwise driven rotary shaft for rotating said carousel for sequentially dropping samples through said slot in said tray, which slot is aligned with a sample-receiving member of an analytical furnace for sequentially receiving samples from said carousel.

10. The carousel as defined in claim 9 wherein said carousel is made of one of metal and a transparent polymeric material.

11. The carousel as defined in claim 10 wherein said mount positions the axis of rotation of said carousel at said second acute angle of about 45° to the furnace.

12. The carousel as defined in claim 11 wherein said cavities are formed at said first acute angle of about 30° to the axis of rotation of said carousel.

13. The carousel as defined in claim 8 wherein said mount includes a drive shaft and said carousel includes a hub for removably mounting said carousel to said drive shaft.

14. A sample handling carousel for an analytical furnace comprising:
   a disk-shaped carousel having an axis of rotation, a beveled outer edge, and a plurality of angularly spaced sample holding cavities, said cavities formed through said beveled outer edge of said carousel and extending outwardly from the axis of rotation of said carousel at a first acute angle;
   a stationary tray positioned below said carousel, said tray including an edge conforming to said beveled outer edge of said carousel and having a slot for allowing an analytical sample to pass therethrough only when one of the sample holding cavities aligns with said slot in said tray, such that the sample is released from said sample holding cavity and enters the furnace; and
   a mounting and drive assembly for said carousel, said assembly including a drive motor and drive shaft coupled to said carousel for rotating said carousel, said assembly mounting said carousel and tray to a furnace at a second acute angle to a horizontal plane, wherein said second acute angle is greater than said first acute angle.

15. The apparatus as defined in claim 14 wherein said carousel and tray include central apertures which are aligned and further including a hub extending through said central apertures for holding said tray and carousel together while allowing rotation of said carousel with respect to said tray.

16. The apparatus as defined in claim 15 wherein said hub engages said drive shaft to rotate said carousel with said drive shaft and wherein said hub is removably mounted to said drive shaft.

17. The apparatus as defined in claim 16 wherein a surface of said carousel facing said tray includes a spring-loaded pin and wherein said tray includes an aperture for receiving an end of said pin for indexing said carousel onto said tray when said tray and carousel are positioned on said hub.

18. The apparatus as defined in claim 17 wherein said carousel includes an annular recess formed in said surface facing said tray and wherein said tray includes an annular shoulder extending into said recess, and wherein one of said recess and shoulder includes an O-ring providing a frictional interface between said carousel and said tray.

19. The apparatus as defined in claim 18 wherein said hub includes a shoulder at one end for engaging a surface of said tray surrounding said central opening and remote from said carousel, and an opposite threaded end which extends through said carousel, and wherein said apparatus further includes a threaded locking ring which extends over said threaded end of said hub and is tightened against said carousel to provide a predetermined rotational friction between said carousel and tray.

20. The apparatus as defined in claim 14 wherein said tray is coupled to said mounting and drive assembly by a locking member to prevent rotation of said tray with respect to said carousel.

* * * * *